United States Patent
Pollack

(10) Patent No.: US 9,456,919 B2
(45) Date of Patent: Oct. 4, 2016

(54) SYSTEM, METHOD, AND DEVICE FOR POSTURE SUPPORT

(71) Applicant: Jeanie Pollack, Chicago, IL (US)

(72) Inventor: Jeanie Pollack, Chicago, IL (US)

(73) Assignee: Jeanie Pollack, Chicago, IL (US)

( * ) Notice: Subject to any disclaimer, the term of this patent is extended or adjusted under 35 U.S.C. 154(b) by 262 days.

(21) Appl. No.: 14/205,705

(22) Filed: Mar. 12, 2014

(65) Prior Publication Data

US 2015/0257914 A1    Sep. 17, 2015

(51) Int. Cl.
*A61F 5/00*    (2006.01)
*A61F 5/02*    (2006.01)

(52) U.S. Cl.
CPC .......... *A61F 5/026* (2013.01); *A61F 2250/001* (2013.01)

(58) Field of Classification Search
CPC ...... A61F 5/3723; A61F 5/3738; A61F 5/34; A61F 5/3746; A61F 5/3753; A61F 13/146; A61F 2007/0086; A61F 5/0118; A61F 5/013; A61F 5/0193; A61F 5/024; A61F 5/026; A61F 5/03; A61F 5/055
USPC ........................... 602/19; 128/874–875; 2/44
See application file for complete search history.

(56) References Cited

U.S. PATENT DOCUMENTS

| | | |
|---|---|---|
| D35,225 S | 10/1901 | Sheldon |
| 766,863 A | 8/1904 | Adams |
| 1,075,348 A | 10/1913 | Fritsch |
| 1,367,420 A * | 2/1921 | Munter .................. A61F 5/026 2/44 |
| 1,562,935 A | 11/1925 | Whisner |
| 3,094,984 A | 6/1963 | Jewett |
| 3,141,456 A | 7/1964 | Meek |
| 3,182,655 A * | 5/1965 | Nelkin .................... A61F 5/026 602/19 |
| 3,338,236 A | 8/1967 | McLeod, Jr. |
| 3,718,137 A | 2/1973 | Gaylord, Jr. |
| 3,857,388 A | 12/1974 | Frankel |
| 3,897,776 A | 8/1975 | Gaylord, Jr. |
| D323,909 S * | 2/1992 | Dewall ..................... D29/101.1 |
| 6,440,094 B1 | 8/2002 | Maas |
| D471,633 S | 3/2003 | Brown |
| 7,578,798 B2 | 8/2009 | Rhee |
| D635,624 S | 4/2011 | Brown et al. |
| D699,365 S | 2/2014 | Pollack |
| 2006/0161082 A1 | 7/2006 | Rhee |
| 2007/0239091 A1 * | 10/2007 | Brockington ......... A61F 5/3723 602/4 |

* cited by examiner

*Primary Examiner* — Michael Brown
(74) *Attorney, Agent, or Firm* — Vedder Price

(57) ABSTRACT

The present invention relates to a new system, method, and device for assisting a user in maintaining proper posture. More specifically, the present invention relates to a new system, method, and device for applying pressure to one or more of a person's posture pressure points when the person has poor posture, for example because the person's body is misaligned.

2 Claims, 3 Drawing Sheets

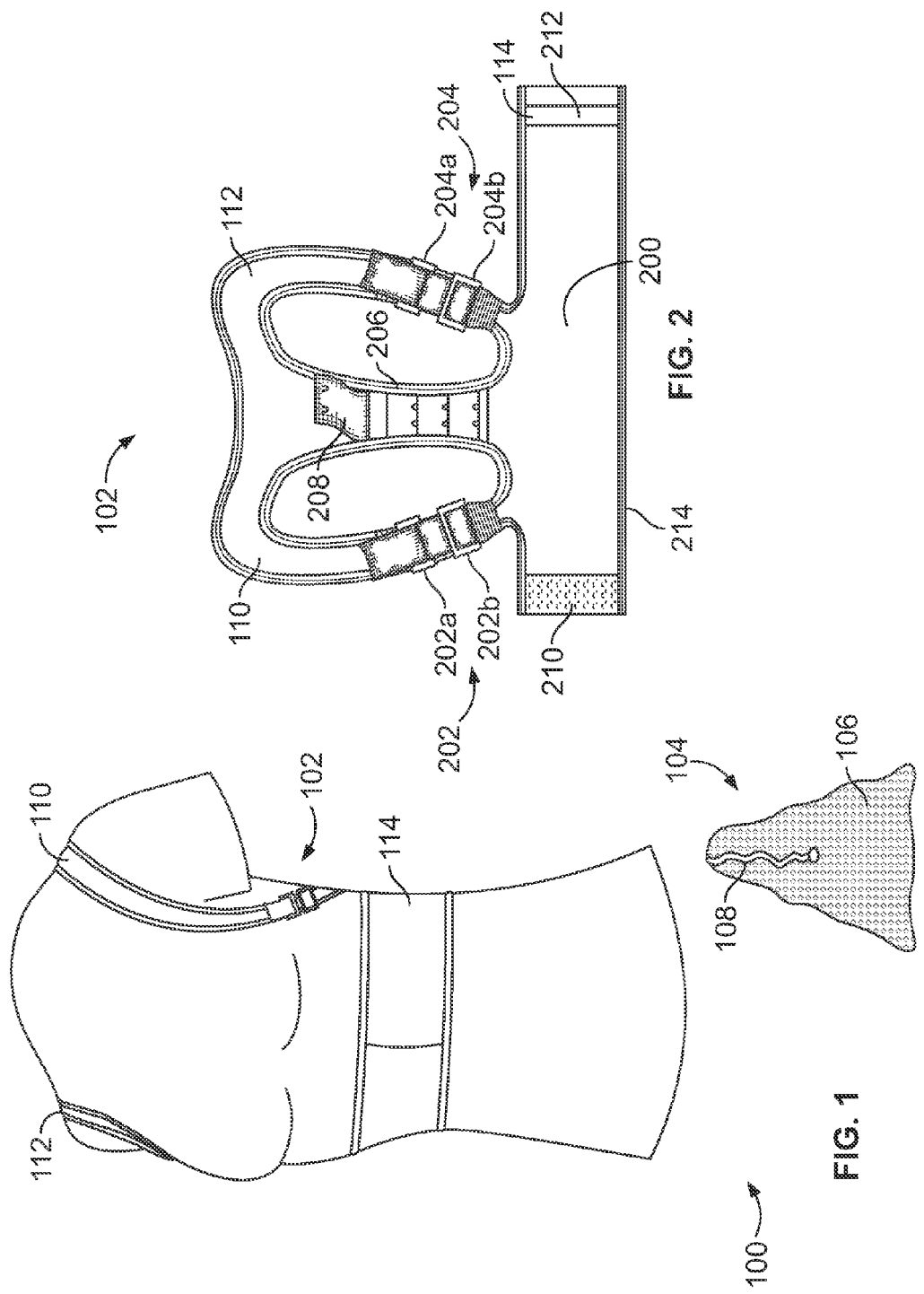

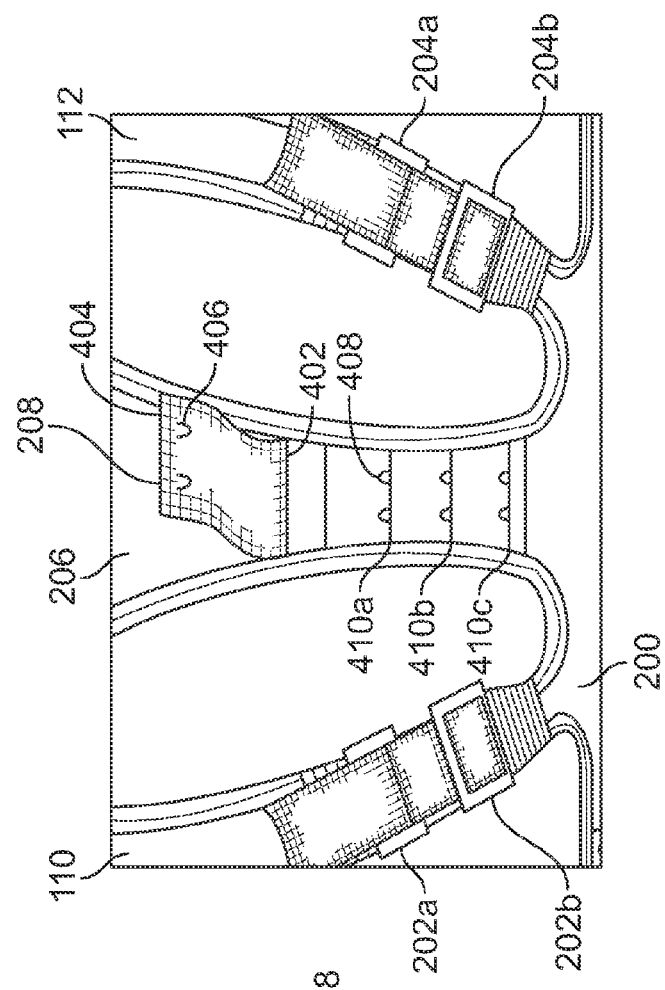
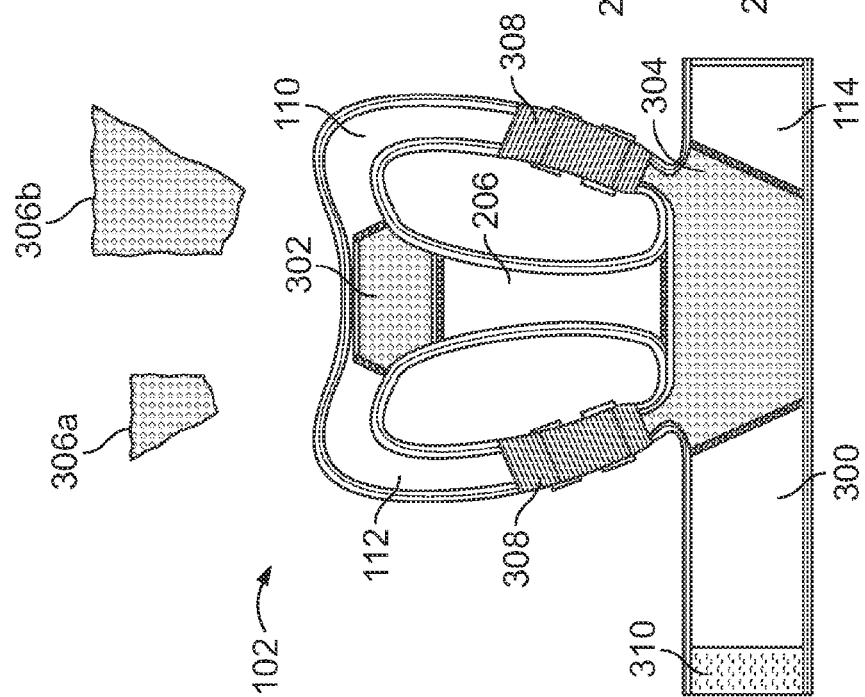

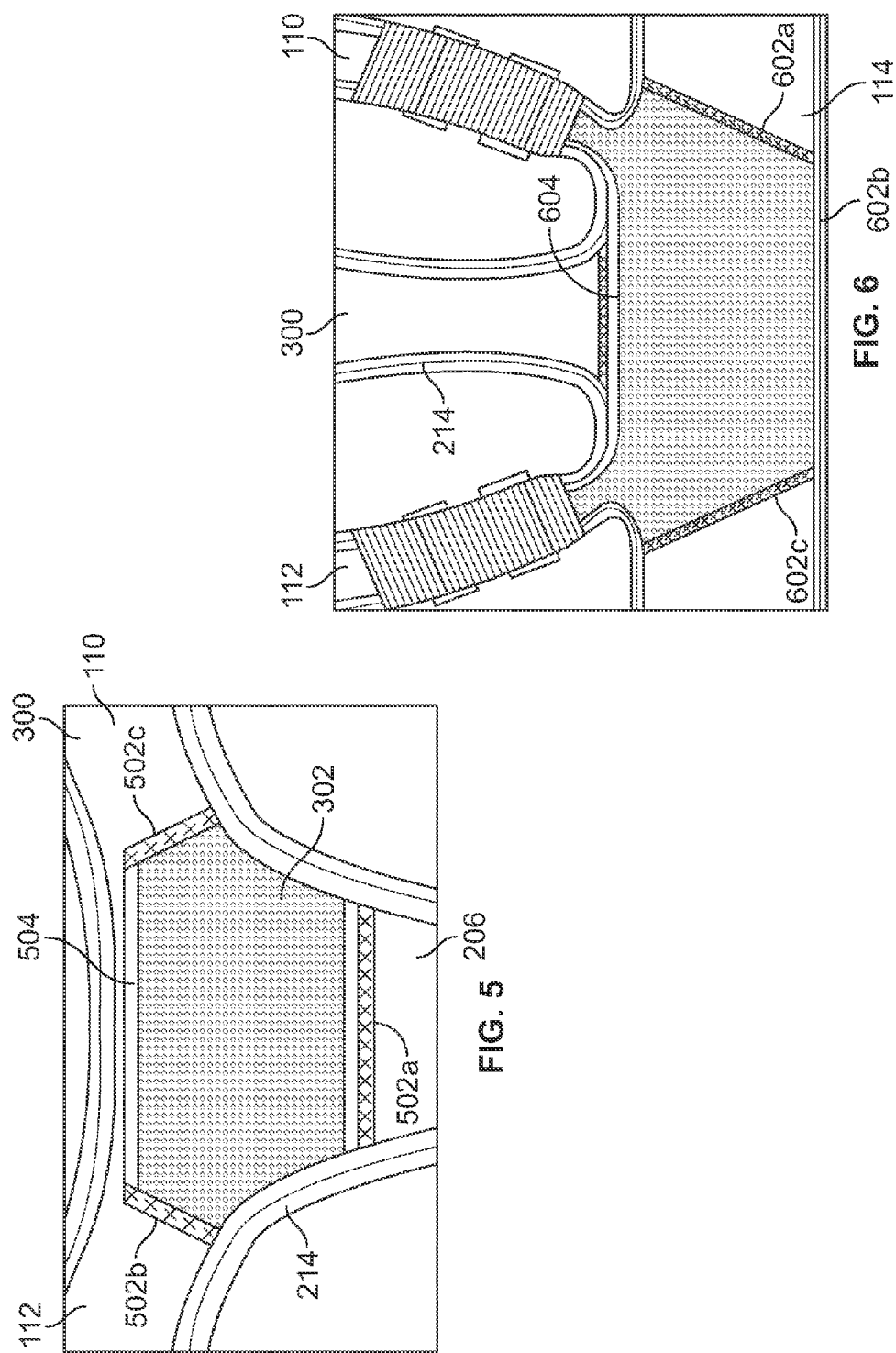

SYSTEM, METHOD, AND DEVICE FOR POSTURE SUPPORT

FIELD OF THE INVENTION

The present invention relates to a system, method, and device for assisting a user in maintaining proper posture.

BACKGROUND OF THE INVENTION

Posture is the arrangement or positioning of the human body in relation to the force of gravity. Posture determines how the force of gravity is distributed throughout the body. Muscles, joints, and ligaments are all stressed by gravity. Poor posture, or improper alignment of the body, may cause excessive stress or fatigue on various body parts. This stress may be felt in many ways. For example, a person suffering from bad posture may feel tired or drained of energy. Furthermore, such a person may suffer from sore or tight muscles or stiff and painful joints. For some people, these afflictions are short-lived, lasting for only a few hours or days. However, if poor posture persists over time, more serious injuries, including arthritis or chronic pain, may result. Furthermore, the negative effects of poor posture may exacerbate over time if the underlying cause—that is, the poor posture itself—is not addressed.

Significantly, the effects of poor posture may not be noticed immediately. As a result, a person may not realize he or she has poor posture until after an injury has already occurred. Furthermore, even after suffering from the symptoms of poor posture, a person may fail to realize the cause of his or her afflictions. This allows the damage to the body to continue to compound, resulting in even more severe injuries over time.

Despite the significant detrimental effects of poor posture, many people either do not know what proper posture is or do not realize it when they begin to have poor posture. For example, an office worker who sits at a desk every day may not realize when he or she begins to slump down in his or her chair, stressing his or her knees, hips, and lower back as they are bent out of alignment. Similarly, a teacher who stands all day may not realize he or she is slouching, stressing the joints and muscles in his or her neck painfully. Even after realizing one occasionally has bad posture, for example, by looking at oneself in a mirror or consulting an ergonomics specialist, a person may be oblivious to future instances of poor posture. Accordingly, there is a need for systems, devices, and methods to help individuals to recognize and correct poor posture.

BRIEF DESCRIPTION OF THE SEVERAL VIEWS OF THE DRAWING

FIG. 1 illustrates a kit in accordance with an embodiment of the present invention, including a posture support being worn by a user and a bag.

FIG. 2 is an illustration of the rear or exterior face of a posture support device according to an embodiment of the present disclosure.

FIG. 3 is an illustration of the front or interior face of a posture support device according to an embodiment of the present disclosure, including two removable cushions.

FIG. 4 is an illustration of a detailed view of the central portion of the rear or exterior face of the device as shown in FIG. 2.

FIG. 5 is an illustration of a detailed view of the top portion of the front or interior face of the device as shown in FIG. 3.

FIG. 6 is an illustration of a detailed view of the bottom portion of the front or interior face of the device as shown in FIG. 3.

DETAILED DESCRIPTION OF THE INVENTION

For the purposes of promoting and understanding the present invention and the principles disclosed herein, reference is now made to the preferred embodiments illustrated in the drawings and specific language used to describe the same. It is nevertheless understood that no limitation of the scope of the present invention is thereby intended. Such alterations and further modifications to the illustrated devices, and such further applications of the principles disclosed as illustrated herein, are contemplated as would normally occur to one skilled in the art to which this disclosure relates.

Described herein are embodiments of a system, device, and method in accordance with the present invention for adjusting the posture of a user. In an embodiment, a device is used to make a user of the device conscious of his or her poor posture. When the user recognizes poor posture, he or she may quickly correct it. Over time, a user may eliminate bad posture habits, such as slouching or slumping, and learn to consistently maintain proper posture. As posture may have a direct impact on health, the device may thereby help users to become healthier.

Good posture requires the proper alignment of the spine. For example, when a person has good posture, his or her spine may be aligned into a gentle s-shaped curve. This curved shape distributes forces throughout the body and avoids excessive stress on any particular muscle, joint, or tendon. To assist a person in obtaining correct alignment, pressure may be applied to "posture pressure points," such as those located at the small of the back and between the shoulders. By applying gentle pressure to these locations, a person receives constant feedback regarding his or her posture and is able to consciously work to maintain correct posture. This feedback allows a person to adjust his or her posture.

With reference to FIG. 1, an embodiment of the present invention includes a kit 100 comprising a device 102 for promoting good posture and a bag 104. In an embodiment, the bag 104 is sized so as to be capable of containing the device 102. In an embodiment, the bag 104 is formed using a sheet of material 106 shaped into a hollow tube surrounding an interior volume. In an embodiment, two opposite ends of the sheet of material may be attached together using stitching. The bag 104 may be sealed at one end, for example, by stitching. The opposite, open end of the bag 104 may be fitted with a closure mechanism 108 to retain the contents of the bag 104. In an embodiment, the closure mechanism 108 is a drawstring that is threaded through the perimeter of the open end of the bag 104. One of skill in the art will recognize that other shapes and forms of bag 104 may be used.

The bag 104 may serve, for example, to store the device 102 during periods of nonuse. In an embodiment, the bag 104 and device 102 are fashioned from machine-washable materials. In an embodiment, the bag 104 is created so as to allow water, soap, and other particulates to readily reach the interior volume of the bag 104. In one embodiment, the bag 104 is constructed using mesh such as, for example, a nylon mesh. In another embodiment, the bag 104 is created from a material that is permeable to water, soap, and particulates. In these embodiments, the device 102 may be placed inside the bag 104 and cleaned using a standard washing machine. This enables the device 102 to be cleaned easily without experiencing excessive wear or otherwise being damaged by the washing machine or by a dryer.

In another embodiment, the bag 104 is constructed from a material that is impermeable to odors. In this way, a device 102 that has been worn or otherwise become dirty may be stored and transported inside the bag 104 without causing any olfactory discomfort to nearby individuals. For example, a factory worker could wear the device 102 during a twelve-hour shift on a hot day before storing the device in the bag 104 for the ride home on the bus. By placing the device 102 inside the bag 104 and closing the bag 104, odors are trapped inside the bag 104. Similarly, an office worker may store the device 102 in the bag 104 between uses at work without causing distress to others who may work nearby.

As further shown in FIG. 1, in an embodiment, the device 102 includes a first shoulder strap 110, a second shoulder strap 112, and a waist strap 114. A person may use the device 102 by placing one arm through the first shoulder strap 110, the other arm through the second shoulder strap 112, and fastening the waist strap 114 around the waist. In an embodiment, the waist strap 114 is made of a wide strip of material that may be fitted around a user's abdominal and lower back regions. In an embodiment, the waist strap 114 provides constant gentle pressure to the small of the back. Similarly, the waist strap 114 provides gentle pressure to the abdominal region.

With reference to FIG. 2, the back or exterior face 200 of the device 102 is shown. In an embodiment, the device 102 includes first strap length adjustors 202 on the first shoulder strap 110 and second strap length adjusters 204 on the second shoulder strap 112 so as to allow the length of the shoulder straps 110, 112 to be adjusted. As shown in FIG. 2, the first strap length adjuster 202 may comprise a first rectangular ring 202a and a second rectangular ring 202b. Similarly, the second strap length adjuster 204 may comprise a third rectangular ring 204a and a fourth rectangular ring 204b. However, the strap length adjustors 202, 204 may take the form of d-rings, ladder locks, tri-glides, buckles, or Velcro. Other adjustment mechanisms may also be used, and such alternatives will be readily apparent to one of skill in the art.

As shown in FIG. 2, the device 102 includes a center strap 206 connected to the waist strap 114 at one end and the first shoulder strap 110 and second shoulder strap 112 at the opposite end. The length of the center strap 206 of the device 102 may also be adjusted. In an embodiment, the length of the center strap 206 may be adjusted using one or more strap length adjustors. In the embodiment shown in FIG. 2, the device 102 includes an adjustment strap 208 for adjusting the length of the center strap 206. The length of the center strap 206 may also be referred to as the "height" of the device 102.

As shown in FIG. 2, in an embodiment, the exterior face 200 of the waist strap 114 includes a closure device 210 at one end. The closure device 210 may be, for example, a strip of Velcro. The closure device 210 serves to allow one end of the waist strap 114 to be removably affixed to a matching closure device on the interior of the opposite end of the waist strap 114. The length, or circumference, of the waist strap 114 may be adjusted using the closure devices 210. As will be clear to one of skill in the art, other closure devices may also be used, such as hooks, a prong and hole combination, or any other closure device.

In an alternative embodiment, the waist strap 114 may be formed from a continuous loop without a closure device. The waist strap may be formed from an elastic material that allows the circumference of the waist strap 114 to be adjusted to fit snugly around a user. In an embodiment, the waist strap 114 may include a strap length adjuster, such as a buckle, so as to allow the length of the waist strap to be adjusted.

The exterior face 200 of the waist strap 114 may include portions that are rigid or semi-rigid. These portions may ensure the waist strap remains flat against a user and does not become bent or folded-over. These portions may further serve to evenly distribute pressure around a user's waist or to focus pressure upon particular areas, such as the posture pressure point located at the small of the back or on the abdominals.

As shown in FIG. 2, in an embodiment, the exterior face 200 of the waist strap 114 includes one or more pockets 212. These one or more pockets 212 may be located at the terminal portion of the waist strap 114. Alternatively, these one or more pockets 212 may be located anywhere on the waist strap 114 or on the first shoulder strap 110 or second shoulder strap 112. These one or more pockets 212 may be sized so as to accommodate personal items belonging to the user of the device 102. For example, one pocket 212 may be sized so as to hold one or more credit cards or identification cards. A pocket 212 may be sized so as to hold paper money, coins, keys, or other items. A pocket 212 may be sized so as to hold a cell phone, personal digital assistant, or other small electronic device.

In an embodiment, the device 102 includes a pocket 212 sized to hold an electronic device, an opening located on the shoulder strap, and a passageway leading from the pocket 212 to the opening. For example, the pocket 212 may be locked below the center strap 206 on the waist strap 114 and the passageway may lead up the waist strap 114, along the center strap 206, and along one or both of the shoulder straps 110, 112 to one or more openings on one or both of the shoulder straps 110, 112. The one or more openings and passageway may be sized so as to accommodate a cord and allow a user to connect headphones to an electronic device stored in the pocket 212. In this way, the user may securely carry an electronic device such as a music player or cell phone in the pocket 212 and use the electronic device to listen to audio without the headphone cord snagging on clothing or nearby objects.

The one or more pockets 212 may be fitted with closure devices, such as buttons or Velcro. Alternatively, the one or more pockets 212 may be made from a semi-rigid material, causing the one or more pockets 212 to remain closed unless pressure is applied by a user.

Stitching 214 may be placed around the perimeter of a portion or all of the device 102, including the waist strap 114, the shoulder straps 110, 112, and the center strap 206. As shown in FIG. 2, this stitching 214 may be placed around substantially all of the device 102. The stitching 214 may serve to increase the strength of the device 102. Additionally, the stitching 214 may serve as a visual cue to assist the user in locating the device 102. For example, if the device 102 is made from a black material and the stitching 214 is made using white thread, the stitching 214 may serve to outline the device 102 and make it more visible to a user when the device 102 is worn over dark clothing. Stitching 214 may also be used to distribute force evenly through the device 102.

With reference to FIG. 3, the front or interior face 300 of the device 102 is shown. In an embodiment, a top pocket 302 may be located where the shoulder straps 110, 112 join the center strap 206. In an embodiment, a bottom pocket 304 may be located where the waist strap 114 joins the center strap 206 and shoulder straps 110, 112. As shown in FIG. 3, the top pocket 302 may be positioned so that the pocket 302 is in contact with the posture pressure point located between the shoulder blades when the device 102 is worn. Similarly, the bottom pocket 304 may be positioned so that the pocket 304 is in contact with the posture pressure point located at the small of the back when the device 102 is worn.

Each pocket may be sized so as to hold a PUSHCUSH™ 306a, 306b. Use of one or more PUSHCUSHES™ 306a, 306b in the device 102 may increase the comfort and wearability of the device 102 while providing support to posture pressure points located between the shoulder blades and in the small of the back.

Each PUSHCUSH™ 306a, 306b may consist of an outer material formed around an interior volume. The outer material may be washable. This interior volume may be filled with an inner material, such as foam padding or batting. This inner material may also be washable. The inner material may be soft. Alternatively, the inner material may be firm. In an embodiment, a user may select from a variety of PUSHCUSHES™ 306a, 306b, each with a different firmness. In this way, a user may customize the pressure applied by the device 102 to his or her posture pressure points by selecting PUSHCUSHES™ 306a, 306b of a desired firmness.

In an embodiment, each PUSHCUSH™ 306a, 306b is inflatable. In this embodiment, the interior volume may be filled entirely with air. This allows a user of the device 102 to adjust the firmness of each PUSHCUSH™ 306a, 306b by inflating or deflating it as needed. In this way, a user may obtain a custom fit without needing to obtain multiple sizes of PUSHCUSHES™ 306a, 306b. The outer material may include a material that is substantially impermeable to air, such as rubber or silicon. Additionally, the outer material may include a layer of padding to increase the comfort of the user of the device 102.

In an embodiment, one PUSHCUSH™ 306a is sized so as to fit the top pocket 302. Similarly, another PUSHCUSH™ 306b is sized so as to fit the bottom pocket 304. In an alternative embodiment, both PUSHCUSHES™ 306a, 306b are identically sized and may fit into either the top pocket 302 or the bottom pocket 304.

In an alternative embodiment, one or more of the pockets 302, 304 may be replaced with integral padding. In an embodiment, this padding is shaped as a hemisphere, with the rounded portion facing towards the user when the device 102 is worn.

In an embodiment, at least a portion of the interior face 300 of the device is covered with a padded material. For example, the interior face of the waist strap or shoulder straps may be covered with a padded material. This padded material may serve to distribute pressure evenly to ensure the comfort of the user.

As shown in FIG. 3, at least a portion of each shoulder strap 110, 112 may be made from an elastic material 308. This allows a user of the device 102 to comfortably move his or her arms and upper body while wearing the device 102. As will be recognized by one of skill in the art, the use of an elastic material 308 will cause the pressure applied to the user's body by the device 102 to increase as the user bends.

For example, while the user has proper posture and has his or her spine aligned correctly, a minimum amount of pressure may be applied by the device 102 to the user. In an embodiment, substantially no pressure is applied while the user has proper posture. In an embodiment, pressure is applied via the PUSHCUSHES™ located adjacent to the user's posture pressure points located at the small of the back and between the shoulders. As the user begins to bring his or her body out of proper alignment, for example by slouching forward, the amount of pressure applied to the user's posture pressure points will increase. This increasing pressure gently alerts the user to his or her bad posture, allowing him or her to correct his or her posture by adjusting his or her position until the pressure is reduced or removed.

As discussed above, in an embodiment where a first closure mechanism 210 is located on the exterior face 200 of the waist strap 114, the matching second closure mechanism 310 may be located on the interior face 300 of the opposite end of the waist strap 114. This closure mechanism may be, for example, a strip of Velcro. As will be understood by one of skill in the art, an alternative fastener, such as a clasp, a hook, or a button, may also be used. The closure mechanisms 210, 310 allow for the adjustment of the circumference of the waist strap 114 when the first closure mechanism 210 is fastened to the second closure mechanism 310.

With reference to FIG. 4, a detailed view of the center strap 206 in an embodiment of the device 102 including an adjustment strap 208 on the center strap 206 for changing the height of the device 102 is shown. A fixed end 402 of the adjustment strap 208 may be permanently attached to the center strap 206, for example, by stitching. The opposite end 404 of the adjustment strap 208 may be left free. One or more first fasteners 406 may be attached to the adjustment strap 208. One or more second fasteners 408 may be attached to the center strap 206 and configured to mate with the one or more first fasteners 406. Alternatively, one or more fasteners may be located only on the adjustment strap 208 or the center strap 206. The fasteners 406, 408 may removably connect the free end 404 of the adjustment strap to the center strap 206. The adjustment strap 208 may be connected in one of a plurality of locations to provide a respective one of a plurality of heights.

As shown in FIG. 4, in an embodiment the fasteners 406 comprise two hooks that are attached to the free end 404 of the adjustment strap 208. The second fasteners 408 comprise one or more rows 410, each consisting of a pair of matching hooks, affixed to the center strap 206. By connecting the hooks 406 on the adjustment strap 208 to the hooks 408 in one row 410 on the center strap 206, the height of the device 102 may be set. As will be clear to one of skill in the art, other fasteners such as Velcro may be used. In an alternative embodiment, the adjustment strap 208 is replaced with a strap length adjuster, such as a buckle.

As further shown in FIG. 4, in an embodiment the strap length adjuster 202 on the first shoulder strap 110 may comprise a pair of buckles 202a, 202b to permit the length of the first shoulder strap 110 to be adjusted. Similarly, the strap length adjuster 204 on the second shoulder strap 112 may comprise a pair of buckles 204a, 204b to permit the length of the second shoulder strap 112 to be adjusted. The length of each shoulder strap 110, 112 may be adjusted independently. By using the adjustment strap 208 to customize the height of the device 102 and the buckles 202, 204 to customize the length of the shoulder straps 110, 112, a user may fit the device 102 perfectly to his body. For example, a user may adjust the fit of the device 102 to ensure that the pockets 302, 304 are aligned adjacent to his posture pressure points and that the desired amount of pressure is applied to each posture pressure point.

Referring to FIG. 5, a detailed view of a portion of the interior face 300 of the device 102 including the top pocket 302 is shown. In an embodiment, the pocket 302 is attached to the device along three sides 502a, 502b, and 502c, leaving an opening 504 on the fourth side. The opening 504 may be located on the top side. The pocket 302 may be attached to the device 102, for example, by stitching. In this way, a PUSHCUSH™ may be securely held in the pocket 302 during normal use. At the same time, a PUSHCUSH™ may be easily inserted or removed from the pocket 302 through the opening 504.

In an embodiment, a closure mechanism such as a zipper or drawstring may be used to seal the opening 504 of the pocket 302. In an embodiment, at least a portion of the other sides 502a, 502b, 502c of the pocket 302 may be left open. For example, in an embodiment, only the corners of the pocket 302 may be affixed to the device 102. In this way, the air flow into the pocket 302 may be increased to assist in distributing heat, such as a user's body heat, away from the device 102.

In an embodiment, the pocket 302 includes a layer of padding. For example, the interior face 300 of the pocket 302 may contain a thin layer of padding to increase the comfort of the user. Similarly, the layer of padding may be located inside the pocket 302. In another embodiment, the pocket 302 or the portion of the device 102 adjacent to the pocket 302 may be made of a mesh material, so as to permit the flow of air into the pocket 302. For example, the exterior face 200 of the device 102 adjacent to the pocket 302 may be constructed of mesh.

As shown in FIG. 5, in an embodiment, stitching 214 may surround the perimeter of the device 102 around the pocket 302. This may increase the strength of the device 102 and ensure the pocket 302 does not become separated from the device 102. In an embodiment, a layer of material forming the center strap 206 and shoulder straps 110, 112 is folded over the material forming the pocket 302. This layer is then attached to the center strap 206 and/or shoulder straps 110, 112 using stitching 214.

The pocket 302 may be constructed of a material that is a different color from that of the material used for the remainder of the device 102. In this way, a user of the device 102 may be provided with a clear visual cue that a PUSHCUSH™ may be placed in the pocket 302. In an embodiment, the pocket 302 and PUSHCUSH™ may be the same color. In another embodiment, the opening 504 of the pocket 302 may be surrounded by stitching. This stitching may optionally be of a different color from that of the pocket 302 or the device 102. In an embodiment, the stitching along the opening 504 of the pocket 302 is the same color as the stitching 214 around the perimeter of the device 102.

The pocket 302 may be sized so as to snugly fit a PUSHCUSH™. In an embodiment, the pocket 302 is made of an elastic material so as to allow it to adjust to snugly contain a PUSHCUSH™. In an embodiment, the elastic material is capable of stretching to snugly accommodate PUSHCUSHES™ of various sizes.

In an alternative embodiment, the pocket 302 may be replaced by a fastener, such as Velcro. In this embodiment, a PUSHCUSH™ may be affixed to the device 102 using the fastener.

Referring to FIG. 6, a detailed view of a portion of the interior face 300 of the device 102 including the bottom pocket 304 is shown. In an embodiment, the pocket 304 is attached to the device along three sides 602a, 602b, and 602c, leaving an opening 604 on the fourth side. The opening 604 may be located on the top side. The pocket 304 may be attached to the device 102, for example, by stitching. In this way, a PUSHCUSH™ may be securely held in the pocket 304 during normal use. At the same time, a PUSHCUSH™ may be easily inserted or removed from the pocket 304 through the opening 604.

In an embodiment, a closure mechanism such as a zipper or drawstring may be used to seal the opening 604 of the pocket 304. In an embodiment, at least a portion of the other sides 602a, 602b, 602c of the pocket 304 may be left open. For example, in an embodiment, only the corners of the pocket 304 may be affixed to the device 102. In this way, the air flow into the pocket 304 may be increased to assist in distributing heat, such as a user's body heat, away from the device 102.

In an embodiment, the pocket 302 includes a layer of padding. For example, the interior face 300 of the pocket 304 may contain a thin layer of padding to increase the comfort of the user. Similarly, the layer of padding may be located inside the pocket 304. In another embodiment, the pocket 304 or the portion of the device 102 adjacent to the pocket 304 may be made of a mesh material, so as to permit the flow of air into the pocket 304. For example, the exterior face 200 of the device 102 adjacent to the pocket 304 may be constructed of mesh.

As shown in FIG. 6, in an embodiment stitching 214 may surround the perimeter of the device 102 around the pocket 304. This may increase the strength of the device 102 and ensure the pocket 304 does not become separated from the device 102. In an embodiment, a layer of material forming the waist strap 114 is folded over the material forming the pocket 304. This layer is then attached to the waist strap 114 using stitching 214.

The pocket 304 may be constructed of a material that is a different color from that of the material used for the remainder of the device 102. In this way, a user of the device 102 may be provided with a clear visual cue that a PUSHCUSH™ may be placed in the pocket 304. In an embodiment, the pocket 304 and PUSHCUSH™ may be the same color. In another embodiment, the opening 604 of the pocket 304 may be surrounded by stitching. This stitching may optionally be of a different color from that of the pocket 304 or the device 102. In an embodiment, the stitching along the opening 604 of the pocket 304 is the same color as the stitching 214 around the perimeter of the device 102.

The pocket 304 may be sized so as to snugly fit a PUSHCUSH™. In an embodiment, the pocket 304 is made of an elastic material so as to allow it to adjust to snugly contain a PUSHCUSH™. In an embodiment, the elastic material is capable of stretching to snugly accommodate PUSHCUSHES™ of various sizes.

In an alternative embodiment, the pocket 304 may be replaced by a fastener, such as Velcro. In this embodiment, a PUSHCUSH™ may be affixed to the device 102 and held in a desired location using the fastener.

In an embodiment, the exterior face 200 of the device 102 is made of one or more exterior materials while the interior face 300 of the device 102 is made of one or more interior materials. For example, the exterior face 200 could be made of mesh, so as to allow heat to easily escape from the device. The interior face 300 could be made from a moisture-wicking material, so as to increase the comfort of the user by cooling the skin and keeping it dry. The space between the exterior face 200 and interior face 300 may be filled with a central material, such as padding. Alternatively, the central material may comprise semi-rigid or rigid members to evenly distribute force across the interior face 300 of the device 102 to increase the user's comfort.

In an embodiment, a perimeter material overlaps at least a portion of the perimeter of the exterior face 200 and the interior face 300 of the device 102. This perimeter material is attached to both the exterior face 200 and the interior face 300 of the device using stitching 214. The perimeter material may be of a different color from that of the rest of the device 102. The perimeter material may serve to strengthen the device 102 or to prevent the fraying of the material used for the exterior face 200 or the interior face 300.

In an embodiment, the device 102 is made from thin materials so as to enable a user to wear the device 102 under a shirt or other clothing. Further, the material of the device 102 may be selected so as to minimize visible lines, such as those caused by seams or bulges, when the device is worn under clothing. In an alternative embodiment, the device 102 is incorporated directly into a shirt that may be worn by the user. For example, a shirt may be configured so that the shoulder straps 110, 112 are incorporated in the shoulders of the shirt, the waist strap 114 is incorporated in the perimeter of the torso of the shirt, and the center strap 206 is incorporated into the back of the shirt. Strap length adjusters, such as adjustment strap 402, may be located on the exterior face of the shirt and function to allow for the shoulder straps 110, 112, waist strap 114, and center strap 206 to be adjusted. In an embodiment, the top pocket 302 and bottom pocket 304 may be attached to the interior face of the shirt.

In an embodiment, the device 102 is physically incorporated into a garment, such as a shirt. The device 102 may be incorporated into a variety of clothing worn on the upper body, including: undergarments such as an undershirt, bra, or camisole; general purpose clothing, such as a t-shirt or dress shirts; or specialized clothing, such as surgical scrubs, aprons, smocks, or personal protective equipment (PPE) worn on the upper-body. Top pocket 302 and bottom pocket 304 may be attached to the interior face of the garment, located so as to be proximate to the user's posture pressure points when the garment is worn. In an embodiment, the shoulder straps 110, 112, waist strap 114, and center strap 206 are separate from but attached to the material of the garment. In an alternative embodiment, the material of the garment itself functions as the shoulder straps 110, 112, waist strap 114, and center strap 206. The garment may come in a variety of sizes so as to allow a user to obtain a good fit.

In an embodiment, the device 102 is incorporated into a garment made from an elastic material. The elastic material used for the garment serves to apply pressure to the user's posture pressure points through the PUSHCUSHES™ 306*a*, 306*b* that may be placed in the pockets 302, 304 as the user's body moves out of alignment. In an embodiment, the garment includes one or more pieces of elastic material that apply greater force when deformed than the elastic material that is used to make the remainder of the shirt. These pieces of elastic may be used in place of the shoulder straps 110, 112, waist strap 114, and center strap 206, so as to increase the rate at which pressure to the user's posture pressure points increases as the user's body moves out of alignment.

In the present disclosure, the words "a" or "an" are to be taken to include both the singular and the plural. Conversely, any reference to plural items shall, where appropriate, include the singular.

It should be understood that various changes and modifications to the presently preferred embodiments disclosed herein will be apparent to those skilled in the art. Such changes and modifications can be made without departing from the spirit and scope of the present disclosure and without diminishing its intended advantages. It is therefore intended that such changes and modifications be covered by the appended claims.

What is claimed:

1. A posture support kit, comprising:
   a bag, made of one or more first machine-washable materials, comprising at least one bag opening and a bag closure mechanism operatively configured to close said at least one bag opening;
   a posture support device, comprising:
   a waist strap, comprising:
   a first strap connector located on the exterior face of a first end of said waist strap, and
   a second strap connector located on the interior face of a second end of said waist strap;
   wherein said first end is opposite said second end, a first closure mechanism comprises a first hook and loop fastener strip, a second closure mechanism comprises a second hook and loop fastener strip, said first closure mechanism is removably connectable to said second closure mechanism, and the length of said waist strap is adjustable using said first and second closure mechanisms;
   a first shoulder strap connected to said waist strap, including a first strap length adjuster comprising a first rectangular buckle and a second rectangular buckle and a first elastic portion;
   a second shoulder strap connected to said waist strap, including a second strap length adjuster comprising a third rectangular buckle and a fourth rectangular buckle an a second elastic portion;
   a center strap, connected to said waist strap, said first shoulder strap, and said second shoulder strap, including a third strap length adjuster comprising:
   an adjustment strap with a fixed end attached to said center strap and a free end;
   a first pair of hooks attached to said free end of said adjustment strap; and
   a second pair of hooks attached to said center strap;
   wherein said first pair of hooks is removably connectable to said second pair of hooks to adjust the height of said posture support device;
   a top pocket, comprising at least one top opening, located proximate to where said first and second shoulder straps connect to said center strap; and
   a bottom pocket, comprising at least one bottom opening, located proximate to where said center strap connects to said waist strap;
   wherein said posture support device is made of one or more second machine-washable materials;
   a top cushion, wherein said top cushion is made of one or more third machine-washable materials and is sized to fit in said top pocket; and
   a bottom cushion, wherein said bottom cushion is made of one or more third machine-washable materials and is sized to fit in said bottom pocket;
   wherein said bag is sized so as to contain said posture support device and said cushion.

2. A method for facilitating good posture for the user of a posture control device comprising a waist strap, a center strap connected to said waist strap, a first shoulder strap connected to said waist strap and said center strap, a second shoulder strap connected to said waist strap and said center strap, a first pocket located proximate to where said first and second shoulder straps connect to said center strap, and a second pocket located proximate to where said center strap connects to said waist strap, said method comprising:
- placing a first cushion in said first pocket;
- placing a second cushion in said second pocket;
- placing said first shoulder strap over said user's left shoulder;
- placing said second shoulder strap over said user's right shoulder;
- placing said waist strap around said user's waist;
- adjusting the length of said first shoulder strap, said second shoulder strap, said center strap, and said waist strap such that said first pocket is positioned proximate to the portion of said user's back located between said user's shoulder blades and said second pocket is positioned proximate to the lumbar region of said user's back;
- wherein when the body of said user is improperly aligned, pressure is applied to said user's back through said first and second cushions, and pressure is applied to said user's abdominal region through said waist strap.

* * * * *